United States Patent [19]

Seon

[11] Patent Number: 5,441,871
[45] Date of Patent: Aug. 15, 1995

[54] MONOCLONAL ANTIBODY REACTIVE TO HUMAN LEUKEMIA AND LYMPHOMA CELLS AND METHODS OF USING SAME FOR DIAGNOSIS AND TREATMENT

[75] Inventor: Ben K. Seon, Williamsville, N.Y.

[73] Assignee: Health Research, Inc., Buffalo, N.Y.

[21] Appl. No.: 880,518

[22] Filed: May 8, 1992

Related U.S. Application Data

[63] Continuation-in-part of Ser. No. 848,911, Mar. 10, 1992, which is a continuation-in-part of Ser. No. 359,505, Jun. 1, 1989, abandoned.

[51] Int. Cl.$^6$ .................. C07K 15/28; G01N 33/574; G01N 33/577
[52] U.S. Cl. ................... 435/7.23; 435/7.24; 435/172.2; 435/240.27; 436/548; 530/388.73
[58] Field of Search ............... 424/9; 435/7.23, 7.24, 435/70.21, 172.2, 240.27, 188; 436/548; 530/388.73, 391.3, 391.7

[56] References Cited

U.S. PATENT DOCUMENTS

| | | | |
|---|---|---|---|
| 4,671,958 | 6/1987 | Rodwell et al. | 424/85 |
| 4,692,405 | 9/1987 | Freedman et al. | 435/7.23 |
| 4,724,212 | 2/1988 | Epstein | 435/240.27 |
| 4,724,213 | 2/1988 | Epstein | 435/240.27 |
| 4,831,117 | 5/1989 | Uckun | 530/388.73 |
| 5,096,810 | 3/1992 | Schwarting et al. | 435/7.23 |
| 5,162,224 | 11/1992 | Banchereau et al. | 435/240.27 |

FOREIGN PATENT DOCUMENTS 0173494 3/1986 European Pat. Off.

OTHER PUBLICATIONS

*Coulter Immunology*, Coulter Corporation, Inc., Hileah, Fla., 1989, pp. 16–20.
Matsuzaki et al, Cancer Rsch., 47; 2160–2166 (1987).
Hara et al, Cancer Rsch., 48; 4673–4680 (1988).
Nairn, Fluorescent Protein Tracing, Churchill Livingston, Edingburgh, 1976 pp. 301–303.
Stdman's Medical Dictionary, 24th Ed., Williams and Wilkins, Baltimore, 1982, pp. 777–778.
Negoro and Seon, Cnacer Rsch., 41; 2973–2976 (1981).
Seon et al, J. Immunol., 127; 2580–2588 (1981).
Seon et al, Proc. Nat. Acad. Sci. USA, 80; 845–849 (1983).
Seon et al, J. Immunol., 132; 2089–2095 (1984).
Haruta and Seon, Proc. Nat. Acad. Sci. USA, 83; 7898–7902.

*Primary Examiner*—David Saunders
*Attorney, Agent, or Firm*—Michael L. Dunn

[57] ABSTRACT

A leukemia lymphoma reactive monoclonal antibody which, relative to normal peripheral blood cells, strongly reacts with one or more leukemia lymphoma cell specimens selected from the group consisting of B non-Hodgkin's lymphoma cells, B chronic lymphocytic leukemia cells, B prolymphocytic leukemia cells, B hairy cell leukemia cells, and B acute lymphoblastic leukemia cells. More specifically, a novel hybrid cell line, designated 2B-4G9, for production of monoclonal antibody specific for a unique cell surface epitope associated with a wide variety of human lymphomas and leukemias is provided. This invention also provides a method for producing the new monoclonal antibody and to diagnostic procedures using the new monoclonal antibody to detect various leukemias and lymphomas. Also disclosed are methods of using the antibody or reactive fragments of the antibody for the treatment of leukemia-lymphoma patients.

4 Claims, 9 Drawing Sheets

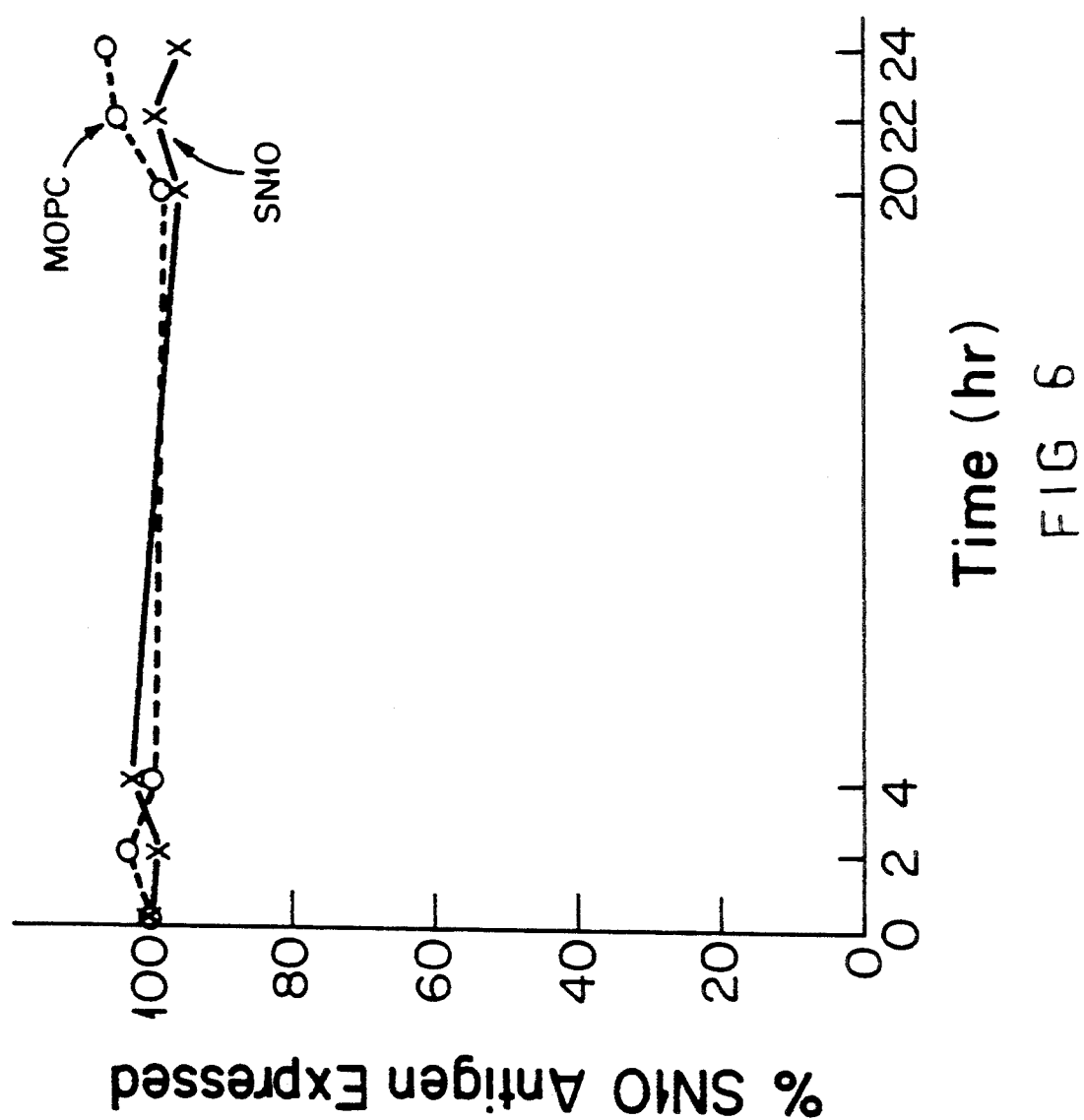

MONOCLONAL ANTIBODY REACTIVE TO HUMAN LEUKEMIA AND LYMPHOMA CELLS AND METHODS OF USING SAME FOR DIAGNOSIS AND TREATMENT

Work relating to the invention described herein was performed under National Institute of Health Grant No. R01 CA 19304. The United States Government may have rights in the invention.

This is a continuation-in-part of U.S. Pat. application Ser. No. 07/848,911, filed Mar. 10, 1992, which is a continuation-in-part of U.S. Pat. application Ser. No. 07/359,505, filed Jun. 1, 1989 and now abandoned.

BACKGROUND OF THE INVENTION

This invention relates to a novel monoclonal antibody (mAb) reactive with a wide variety of human leukemias and lymphomas, to a novel monoclonal antibody generated from a novel hybridoma cell line, and to methods of using the monoclonal antibody, in whole or in part, for the diagnosis and therapy of various human leukemia-lymphomas (LL).

During the last few decades, considerable improvement in the therapy of various forms of human LL has been achieved primarily because of the successful application of chemo-radiotherapy (e.g., reviewed in DeVita et al., Cancer Res. 47, 5810–5824 [1987]). However, many forms of LL are still associated with poor prognosis. These LL include low-grade NHL, prolymphocytic leukemia, B ALL, acute myelogenous leukemia, and chronic myelogenous leukemia. In this regard, there still exists a strong need for the development of a new modality for treating LL.

Recently, several mAbs directed toward LL associated antigens have been shown to be useful for diagnosis and follow-up of LL (Foon et al., Blood, 68: 1–31 [1986]). However, few, if any, anti-LL mAbs were clearly shown to be effective in the in vivo therapy (serotherapy) of LL. Therefore, the generation and characterization of new effective anti-LL mAbs are valuable.

A promising approach to the serotherapeutic utilization of anti-LL mAbs is to target LL cells by conjugating a mAb with an appropriate cytotoxic agent such as chemotherapeutic drugs, toxin subunits, or radioisotopes (reviewed in Ghose et al., J. Natl. Cancer Inst. 61: 657–676 [1978]; Vitetta et al., Science [Washington, D.C.] 238: 1098–1104 [1987]; Seon et al., New Horizons in Tumor Immunology, pp. 329–348, Amsterdam Elsevier Science Publishers [1989] and Order et al., Cancer Res. [Suppl.] 50 10115–10135 [1990]). The tumor specificity of the mAb is of paramount importance in the preparation of an effective immunoconjugate of an anti-LL mAb. In addition, a high binding of the mAb to target antigen and a relatively abundant target antigen on the cells are important. Furthermore, in most cases, the mAb needs to be effectively internalized into the target cells after binding to the cell surface antigen. However, antibody binding to the target antigen should not induce a strong down-regulation of antigen expression (Luo et al., J. Immunology, 145: 1974–1982 [1990]).

BRIEF DESCRIPTION OF THE INVENTION

The invention comprises a leukemia lymphoma reactive monoclonal antibody which, relative to normal peripheral blood cells, strongly reacts with one or more leukemia lymphoma cell specimens selected from the group consisting of B non-Hodgkin's lymphoma cells, B chronic lymphocytic leukemia cells, B prolymphocytic leukemia cells, B hairy cell leukemia cells, and B acute lymphoblastic leukemia cells.

A specific embodiment of the monoclonal antibody is SN 10, produced by hybridoma cell line 2B-4G9.

The invention further comprises the monoclonal antibody which is directly or indirectly attached or complexed with a compound having a site suitable for attachment or complexing therewith which compound is selected from the group consisting of drugs, toxins or fragments thereof, growth suppressing biological response modifiers, enzymes, liposomes, radioactive agents, photodynamic agents and antibodies.

And the invention includes the methods for using the antibody for detecting and treating leukemia/lymphoma disease.

Methods for preparation of the antibody and kits containing the same are also within the scope of the invention.

DETAILED DESCRIPTION OF THE INVENTION

This invention comprises a novel monoclonal antibody (mAb) as previously described, a preferred embodiment of which has been designated SN10, and which meets the five important requirements stated above for preparing a potentially effective immunoconjugate. "Monoclonal antibody" and fragments thereof, as used herein is intended to include reactive fragments of the antibody, e g $F(ab')_2$, Fab', Fab, Fv, Fd' and Fd fragments. Furthermore, SN10 meets another important requirement for preparing an effective immunoconjugate, i.e., no significant amount of circulating SN10 antigen was detected in the plasma of LL patients and healthy individuals. The lack of circulating antigen will facilitate targeting the tumor cells in vivo by a mAb. In addition, mAb SN10 reacts with a relatively wide range of leukemia-lymphomas (LL). The availability of a sufficiently large candidate patient population for clinical trials are important for developing a mAb and an immunoconjugate.

Thus, the SN10 mAb appears to have good potential for serotherapy as well as for diagnosis of LL. This mAb was generated by using an antigen preparation which was isolated by established novel procedure (Seon et al., J. Immunology, 127, 2580–2588 [1981] and Negoro et al., Cancer Research 41, 2973–2976 [1981]).

The monoclonal antibody termed SN10 (IgG1-$\kappa$) which was generated and characterized in accordance with the present invention, shows a highly selective reactivity with fresh (uncultured) human leukemia-lymphoma cells. The antigen defined by SN10 is a cell surface glycoprotein composed of a single polypeptide chain of $M_r 36,000$ and designated as gp36.

The primary reactivity of SN10 is against mature B-lineage leukemia-lymphoma cells. For instance, SN10, relative to normal peripheral blood cells, strongly reacted with all of the 17 B non-Hodgkin's lymphoma (NHL) specimens, all of the 15 B chronic lymphocytic leukemia (CLL) specimens, both of the 2 B prolymphocytic leukemia (PLL) specimens, all of the 3 B hairy cell leukemia (HCL) specimens, and 2 of the 3 B acute lymphoblastic leukemia (ALL) specimens tested.

Of normal peripheral blood cells, only a marginal reactivity (low reactivity) of SN10 was detected with a minor subpopulation (<1–4% among different specimens) of isolated B-cells from healthy donors. No significant reactivity of SN10 was detected against any other isolated normal peripheral blood cells which include T-cells, granulocytes, monocytes, erythrocytes, and platelets. The reactivity with normal peripheral blood cells is less than one-half and usually less than one-tenth of the reactivity with reactive B-lineage leukemia-lymphoma cells, as discussed in the previous paragraph. Furthermore, no significant reactivity of SN10 was detected against normal bone marrow specimens.

SN10 has a lower reactivity with normal peripheral blood cells than SN7, as described in co-pending U.S. patent application Ser. No. 07/848,911, filed Mar. 10, 1992 and does not react as well as SN7 with non T/non B lymphoblastic leukemia cells.

In immunohistological studies using frozen tissue sections, SN10 reacted well with malignant lymphomas and showed varying patterns of reaction with hyperplastic reactive lymph nodes. Various normal human tissues tested were unreactive with SN10.

In general, glycoprotein 36 (gp36) was more abundantly expressed on fresh (uncultured) leukemia-lymphoma cells than on cultured leukemia-lymphoma cell lines.

No significant amount of circulating SN10 antigen was detected in the plasma of leukemia-lymphoma patients or normal healthy donors.

Scatchard plot analysis of direct binding of radiolabeled SN10 to LL cells showed that SN10 possesses a high binding avidity to LL cells.

Numerous methods have been employed during recent years for attaching or conjugating a variety of molecules to various sites on antibodies and in particular monoclonal antibodies directed against any desired target antigen. One such method is disclosed in U.S. Pat. No. 4,671,958, the disclosure of which is incorporated by reference herein. The monoclonal antibody of the present invention has been found to be sufficiently stable to undergo known conjugation procedures with other agents. Numerous bioactive agents may be conjugated to the mAb in accord with the present invention including drugs, toxins or toxin fragments, growth modifying biological response modifiers, enzymes, liposomes, radioisotopes, photodynamic agents, or other antibodies including anti-idiotype antibodies, chimeric antibodies and monoclonal antibodies or fragments of such antibodies. In addition, the mAb or fractions of these mAbs may be incorporated into other matrices for use in separation schemes which are based upon antibody-antigen reactions. A multitude of known carrier or conjugating agents is disclosed in U.S. Pat. No. 4,671,958 and any of these agents would be suitable for binding to the antibodies disclosed herein or to active fragments of the antibody, i.e., certain IgG1-$k$ fragments, which show no significant loss of antibody activity.

Numerous drugs may be complexed with the antibody of the present invention. In general, when such drugs are used for detecting or treating leukemia or lymphoma cells, such drugs are cytotoxic agents such as methotrexate as for example described by Endo et al., Cancer Res., V. 48, pp 3330–3335, Jun. 15, 1988 or daunorubicin as for example described by Biddle et al., Leukemia Res., V. 13, No. 8, pp 699–707, 1989; both of which are incorporated herein by reference.

The antibody of the present invention may similarly be complexed with toxins, desirably those which are especially effective against cancer cells, by methods well known to those skilled in the art. The antibody may, for example, be complexed with Pseudomonas exotoxin by methods similar to those described by Fitzgerald et al., Proc. Natl. Acad. Sci. USA, Vol. 84, pp 4288–4292, June 1987, incorporated herein by reference or for example with Ricin or the Ricin A chain fragment, as subsequently described herein.

The antibody of the present invention may be complexed with growth modifying biological response modifiers, especially those which suppress cell growth when the complex is to be used in cancer treatment. Such biological response modifiers may be broadly considered to have hormone-like activity and as such may be broadly classified as hormones. Suitable biological response modifiers or hormones for forming such complexes with antibodies are known to those skilled in the art and for example include interleukins, interferons, growth factors, and lymphokines. Such complexes have utility in cancer management as aids for both cell targeting and growth control.

Methods for forming such complexes are, for example, with respect to interleukin 2, described by Fell et al., Journal of Immun., 146, pp 2446–2452, Apr. 1, 1991, and with respect to growth factors such as TNF, described by Foon, Cancer Res., 49, 1621–1639. Both of these articles are incorporated herein by reference.

Complexes may be formed between the antibody of the present invention and radioactive agents. Methods for forming complexes between antibodies and radioactive agents are well known and an example of such a method is subsequently described herein.

Complexes may also be formed between enzymes and the antibody of the invention. Alkaline phosphatase and cytosine phosphatase enzymes suitable for forming complexes with antibodies are, for example, described by Senter, FASEB Journal, Vol. 4, pp 188–193, February 1990, incorporated herein by reference.

The antibodies of the present invention may be complexed with photodynamic agents. Methods for complexing antibodies with photodynamic agents are well known in the art. Methods for forming complexes with photodynamic agents such as porphorins are, for example, described by Jiang et al., Journal Natl. Can. Inst., Vol. 83, pp 1218–1219, September 1991, incorporated herein by reference.

The antibody of the present invention may be complexed with other antibodies or fragments to increase targeting ability (bispecific antibodies) or to utilize the additional antibody to achieve a desired cancer cell response, e.g., to more efficiently bring cytotoxic T cells to tumor cells. Methods for forming complexes between antibodies are well known in the art. Such a method, with respect to formation of a bispecific antibody is, for example described by Forger et al., Immun. Today, Vol. 12, pp 51–53, 1991, incorporated herein by reference. These methods apply regardless of the source of the antibody or fragment. For example, as later additionally discussed herein, anti-idiotype antibodies and fragments, chimeric antibodies and fragments, and monoclonal antibodies or fragments may be complexed with the antibody of the present invention using generally known complexing methods.

"Fragments" as used herein means a section of a larger intact antibody, which section continues to contain desired recognition sequences. Such fragments in that sense may, in themselves, be considered antibodies and the term "antibody" may be considered to include such fragments. The term "antibody" is also intended to encompass antibodies and fragments of broad source and type, e.g., monoclonal antibodies and fragments, anti-idiotype antibodies and fragments and chimeric antibodies and fragments.

MAb SN10 has been conjugated with the A chain of ricin, a plant toxin. Procedures for forming the conjugate include covalently attaching or complexing the mAb or a fragment thereof to the agent or drug of interest either directly or indirectly using a suitable linking agent. Other mAbs, SN1, SN2, SN5, SN6, and SN7, also identified by the inventor herein, when conjugated with the ricin A-chain (RA), have demonstrated highly specific killing capability for leukemia cells as reported in Cancer Research 44:259–264 (1984), Proc. Natl. Acad. Sci. USA 84:3390–3394 (1987), and Cancer Research 48:4673–4680 (1988), the disclosures of which are incorporated by reference herein. Such conjugated SN1, SN2, SN5 and SN6 MAbs have been found to be effective against T or non-T/non-B leukemia cells, but not against B leukemia lymphoma cells. SN7 conjugate is effective against B leukemia lymphoma cells, but activity against normal cells is higher than desired. SN10 is reactive against B type leukemia and lymphoma cells with low reactivity against normal peripheral blood cells.

Ricin A chain conjugate of SN10 killed leukemia-lymphoma cells effectively, whereas the same conjugate showed no cytotoxicity against control cells. Thus, SN10 bound to target antigen on the cell surface was effectively internalized into the cell.

The results obtained suggest the potential of SN10 for therapy as well as for diagnosis of various forms of leukemia-lymphoma, particularly mature B-lineage leukemia-lymphoma.

The monoclonal antibody SN10 can be generated from a novel hybrid cell line (called "hybridoma") designated 2B-4G9.

BRIEF DESCRIPTION OF THE FIGURES

FIGS. 3A–3D. Reactivity of SN10 with lymphomatous and reactive lymph nodes as determined by immunohistochemical staining. FIG. 3A, Follicular small cleaved cell lymphoma: SN10 reactivity is confined to the majority of the lymphocytes within the neoplastic follicles. The interfollicular areas are essentially negative. FIG. 3B, Negative isotype matching control IgG with the same lymph node (as a); focal reaction due to endogenous peroxidase in the interfollicular histiocytes is noted. FIG. 3C, Diffuse small cleaved cell lymphoma: the majority of the lymphocytes are SN10 positive. FIG. 3D, Reactive lymphoid hyperplasia; the majority of follicular mantle zone lymphocytes are SN10 positive. Sparse to moderate numbers of SN10 positive cells are also noted within the germinal center and interfollicular areas (frozen sections; x 240).

FIG. 6. Regulation of gp36 expression on DND-39 cells which have been incubated with mAb SN10. gp36 expressing DND-39, an American Burkitt's lymphoma cell line, was incubated with an excess of purified mAb SN10 for varying periods. gp36 on the incubated cells was determined by a cellular RIA (see Components and Procedures for Reactions and Testing).

DETAILED DESCRIPTION OF THE INVENTION

Figure 1:
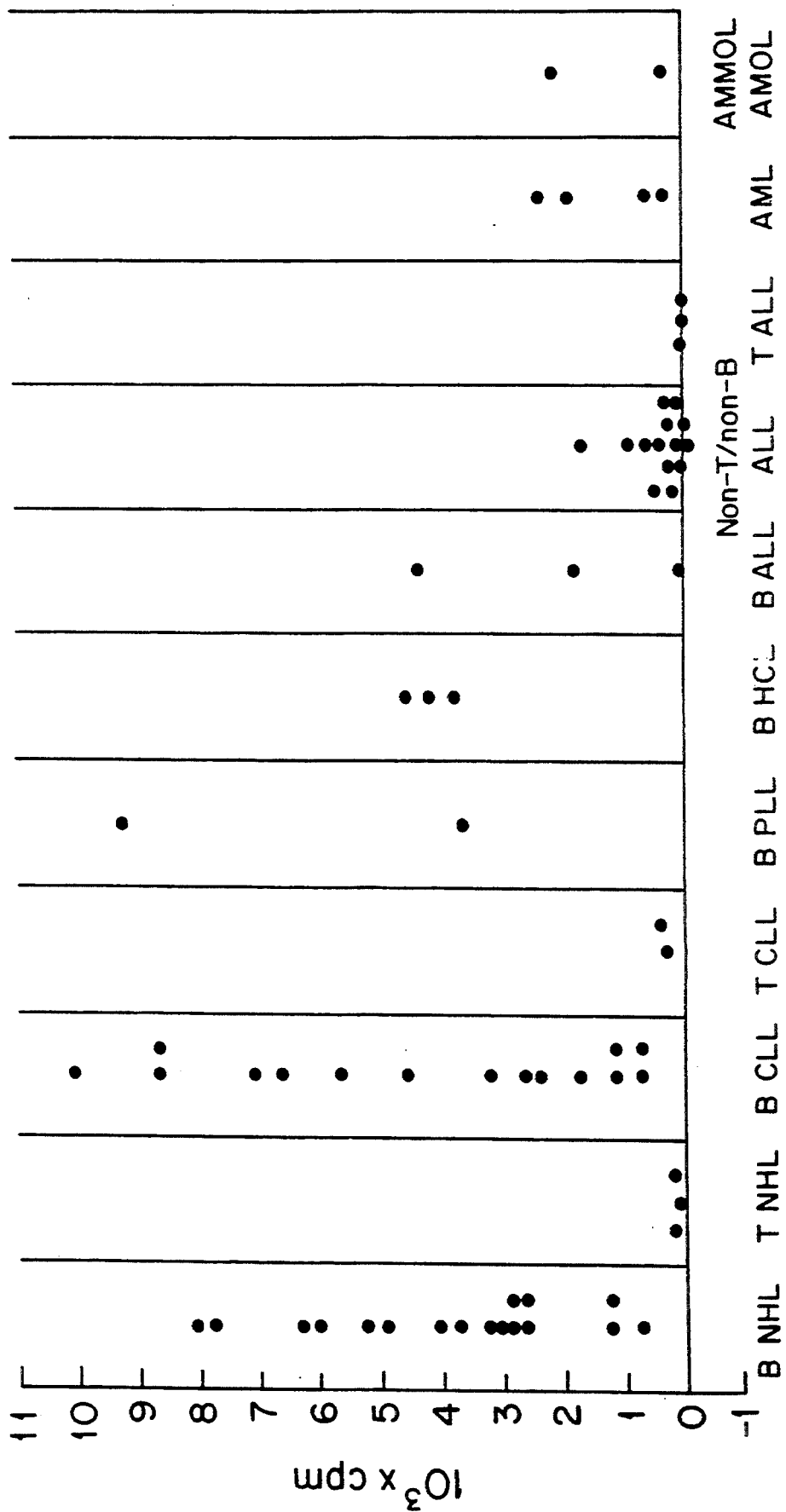
FIG. 1. Reactivity of SN10 with fresh (uncultured) LL cells as determined by a cellular radioimmunoassay (RIA). Individual cell specimens were derived from peripheral blood, bone marrow aspirates, or lymph nodes of 68 different LL patients. In the cellular RIA, three different controls were included with each test sample (Seon et al., J. Immunology, 132, 2089–2095 [1984]). One of these was control mouse IgG1 (10 μg/ml) in the hybridoma culture medium in place of the culture fluid of hybridoma SN10. Radioactivity counts of this control were substracted from those of individual test samples in each test. The other two controls were a positive cell line and a negative cell line in place of the target cell specimen. Pre-B ALL was included in the group of non-T/non-B ALL (acute lymphoblastic leukemia) in the figure. Abbreviations: NHL, non-Hodgkins lymphoma; CLL, chronic lymphocytic leukemia; PLL, prolymphocytic leukemia; HCL, hairy cell leukemia; AML, acute myelocytic leukemia; AMOL, acute monocytic leukemia; AMMOL, acute myelomonocytic leukemia.

The abbreviations used herein are as follows: LL, leukemia-lymphoma; NHL, non-Hodgkin's lymphoma; ALL, acute lymphoblastic leukemia; CLL, chronic lymphocytic leukemia; mAb, monoclonal antibody; RIA, radioimmunoassay; FACS, fluorescence activated cell sorter; LcH, *Lens culinaris* lectin; SDS, sodium dodecyl sulfate; PAGE, polyacrylamide gel electrophoresis; gp36, $M_r 36,000$ glycoprotein defined by SN10; EB, Epstein-Barr; RA, ricin A chain.

The antibody SN10 was generated, in one embodiment of the invention, by using an antigen preparation which was isolated by established procedures disclosed by B. K. Seon et al. in J. Immunology 127:2580 to 2588 (1981).

Antigen Preparation Used for Generating MAbs.

Antigen preparation was isolated from the cell membranes of an approximately equal mixture of NHL cells derived from two patients with B cell type NHLs, i.e., nodular poorly differentiated lymphocytic lymphoma and small lymphocytic lymphoma. This was the first time an antigen preparation was isolated from NHL tissues using our previously disclosed novel procedures. The procedures involved are based on our earlier methods for isolating leukemia antigen preparations (Seon et al., J. of Immunology, 127, 2580–2588 [1981] and Negoro et al., Cancer Res. 41, 2973–2976 [1981]). A brief description of the present isolation system is given below. Cell membranes were isolated from the NHL cells, and the cell membrane antigens were solubilized by deoxycholate treatment. The solubilized antigens were fractionated by affinity chromatography on serially connected columns of LcH and *Ricinus communis* lectin. The LcH-bound and *Ricinus communis* lectin-bound glycoconjugates (mostly glycoproteins) were individually eluted. The LcH-bound and eluted glycoproteins were further subjected to passive immunoaffinity chromatography (Seon et al., Proc. Natl. Acad. Sci. USA, 80, 845–849 [1983] and Haruta et al., Proc. Natl. Acad. Sci. USA, 83, 7898–7902 [1986]) by passing the glycoproteins through three serially connected immuoadsorbent columns. These immunoadsorbents consist of anti-MHC class I antigens mAb (B3-3D1) coupled to Sepharose CL-4B, anti-MHC class II antigens mAb (G4-3A7) coupled to Sepharose CL-4B, and rabbit anti-human peripheral blood lymphocyte antibodies coupled to Sepharose CL-4B. Materials in these pass through fractions were pooled and concentrated.

Generation of MAbs.

Monoclonal antibody was generated by immunizing a BALB/c mouse with the isolated antigen preparation. Immunization of the mouse was carried out as previously described in Seon et al., Proc. Natl. Acad. Sci. USA, 80, 845–849 (1983). Cell fusion, hybridoma screening, cloning, and mAb class determination was carried out as described in Seon et al., Proc. Natl. Acad. Sci. USA, 80, 845–849 (1983) and Seon et al., J. Immunology, 132, 2089–2095 (1984), all of which are incorporated herein by reference as background information.

Components and Procedures for Reactions and Testing.

Cells.

Various established human cell lines were cultured in RPMI 1640 medium supplemented with 4–8% fetal bovine serum, penicillin (100 units/ml), and streptomycin (50 µg/ml) as described previously (Seon et al., Natl. Acad. Sci. USA, 80, 845–849 [1983] and J. Immunology, 132, 2089–2095 [1984]). Fresh (uncultured) cell and tissue specimens from patients with various LLs were kindly provided by the clinics of our institute. Normal (or nearly normal) bone marrow specimens were from patients who were in remission and had a morphologically normal bone marrow. Mononuclear cells were isolated from the bone marrow aspirates by Ficoll-Hypaque gradient centrifugation.

B-cells, T-cells, granulocytes, monocytes, erythrocytes, and platelets of normal peripheral blood from healthy volunteers were isolated as previously described in Seon et al., Proc. Natl. Acad. Sci. USA, 80, 845–849 (1983) and Haruta et al., Proc. Natl. Acad. Sci. USA, 83, 7898–7902 (1986).

Control Murine MAbs, Control Murine IgG, and Reagents.

Leu 16 (anti-CD20 mAb; IgG1) and anti-HLA-DR mAb ($IgG_{2a}$) were purchased from Becton Dickinson (Mountain View, Calif.). Anti-human immunoglobulin λ chain mAb (IgG1) was obtained from AMAC, Inc. (Westbrook, Me.). Control murine IgG (MOPC 195variant; IgG1) was prepared in our laboratory.

L-[$^3$H]leucine and leucine-free medium were purchased from ICN Biomedicals, Inc. (Irvine, Calif.) and GIBCO Laboratories (Grand Island, N.Y.), respectively. Ricin A chain was obtained from Inland Laboratories (Austin, Tex.).

Cellular RIA and FACS Analysis.

Details of the cellular RIA which was used for determining reactivity with mAbs and various cultured and uncultured cells were described in Seon et al., Proc. Natl. Acad. Sci. USA 80, 845–849 (1983) and J. Immunol., 132, 2089–2095 (1984). It should be noted that Fc receptors on the target cells are blocked with human IgG during the assay. In selected cases, the reactivity of mAbs with various cell specimens was also determined by FACS analysis. FACS analysis was carried out as described previously (Luo et al., Cancer Res. 49, 706–710 [1989]). Briefly, one million cells were suspended in 10–20 µl of RPMI 1640 medium containing 25 mM 4-(2-hydroxyethyl)-1-piperazineethanesulfonic acid, 0.1% human IgG, 0.5% bovine serum albumin, 2 mM EDTA, Trasylol (50 kallikrein units/ml), and 0.1% $NaN_3$ and were allowed to stand for 30 minutes at 4° C. Then, the cells were incubated with 100 µl of hybridoma culture supernatant or an isotype matching control mouse IgG solution (10 µg/ml) for 90 minutes at 4° C. After three washes with cold phosphate buffered saline, the cells were incubated with fluorescein-conjugated F(ab')$^2$ fragment of sheep anti-mouse immunoglobulin (Sigma Chemical Co., St. Louis, Mo.) for 90 minutes at 4° C. The incubated cells were washed three times with cold phosphate buffered saline and fixed with formaldehyde. The fixed cells were analyzed by FACS using a Becton Dickinson FACS 440.

Immunohistochemical Staining.

Malignant NHL lymph nodes and various normal human tissues were frozen, sectioned, and fixed in acetone at 4° C. and for 5 minutes as described by Barcos et al. (Leuk. Res., 7, 523–537 [1983]). The fixed tissue sections were stained using Sigma ExtrAvidin staining kits (EXTRA-2) by the avidin-biotin-peroxidase complex procedure following the manufacturer's directions.

Radioimmunoprecipitation and SDS-PAGE.

Three LcH-bound glycoprotein preparations were isolated from the cell membranes of fresh (uncultured) malignant cells from a B CLL patient, a B prolymphocytic leukemia patient, and two B NHL patients, as described above.

The three glycoprotein preparations (a CLL, a prolymphocytic leukemia, and an NHL preparation) were separately radiolabeled with $^{125}$I using an IODO-GEN coated Minisorp tube as described previously in Haruta et al., Proc. Natl. Acad. Sci. USA, 83, 7898–7902 (1986). The three radiolabeled preparations were used separately for immunoprecipitation as described previously. The immunoprecipitation in the present experiment was carried out using Pansorbin coated with affinity purified rabbit anti-mouse IgG antibodies and mAb SN10 (IgG1), isotype matching control mouse IgG (MOPC 195variant) or control mAbs. The specific and control immunoprecipitates were washed as previously described. The radiolabeled antigens in the washed immunoprecipitates were released from the Pansorbin by boiling for 3 minutes in the presence of 2.5% SDS and in the presence or absence of 0.1M dithiothreitol. The released antigens were analyzed by SDS-PAGE as described before and an autoradiograph was prepared by using a Kodak X-OMAT AR film and X-Omatic intensifying screen as previously described in Matsuzaki et al., Cancer Res. 47, 4283–4286 (1987).

Enzyme Treatments of Cell Surface Antigens.

SN10 antigen (gp36) expressing lymphoma cells were treated with various enzymes as described in Seon et al., Mol. Immunol., 23, 569–580 (1986). gp36 remaining on the treated cells was determined using a cellular RIA as before.

Determination of Antigen in the Plasma of LL Patients.

A previously reported solid phase RIA was used with a modification (Matsuzaki, J. Immunol. Methods, 81, 55–63 [1985]). Briefly, 50 μl, in triplicate, of serial dilutions of plasma from healthy donors (control), B NHL patients, and B CLL patients was incubated at 4° C. overnight in the individual wells of 96 well microtiter plates. Then, 50 μl of a 1.6% bovine serum albumin solution in Tris buffer was added and the incubation continued for 1 hour at room temperature. The Tris buffer consisted of 20 mM Tris-HCl, pH 7.0, containing 0.13M NaCl, 2 mM EDTA, 0.03% NaN$_3$ and Trasylol (20 kallikrein units/ml). After the incubation, the wells were washed 3 times with Tris buffer containing 0.2% bovine serum albumin. The wash was followed by adding 100 μl of hybridoma culture fluid, or an appropriate dilution of control mAb or control IgG, and then incubating at 4° C. for 1 hour. After the wells were washed, $^{125}$I labeled F(ab')$_2$ of affinity purified goat anti-mouse IgG antibodies which had been adsorbed with human IgG coupled to Sepharose CL-4B was added and incubated for 1 h at 4° C. The wells were washed and cut out, and the radioactivity was counted in a γ-ray spectrometer.

MOPC 195variant (IgG1) and anti-human immunoglobulin λ chain mAb (IgG1) were included in the test as an isotype matching negative and a positive control, respectively.

A titration experiment showed that in the above described solid phase RIA, we can detect SN10 antigen (gp36) contained in as little as 1 μg of total crude cell membrane protein preparation from B NHL cells.

Direct Binding of $^{125}$I Labeled MAb to LL Cells and Scatchard Plot Analysis.

The equilibrium constant between $^{125}$I labeled SN10 and a fresh (uncultured) B CLL cell specimen, a fresh B NHL cell specimen, or DND-39 (an American Burkitt's lymphoma cell line) cells was determined as described by Trucco et al. (Hum. Immunol. 3, 233–243 [1980]). The radiolabeling of the purified mAb SN10 was carried out by a method using IODO-GEN (see above). Scatchard analysis of the binding data was carried out as previously described above. An equilibrium constant and an average maximal number of mAbs bound/cell were estimated by this analysis.

Regulation of Antigen Expression.

Antigenic modulation and down regulation of gp36 was studied by incubating gp36 expressing DND-39 cells for varying times at 37° C. with an excess of SN10 or an isotype matching control IgG (MOPC 195variant; IgGL$_k$) following a previously described procedure (Luo et al., J. Immun. 145, 1974–1982 [1990]). A preliminary titration experiment showed that 10 μg of purified SN10 mAb/1×10$^6$ DND-39 cells represents antibody excess. The gp36 on the incubated cells was determined by an indirect cellular RIA after appropriate washings of the cells as described previously. In the indirect RIA, SN10 was freshly added to the SN10 or control IgG treated cells and incubated for 1 hour at 4° C. followed by washings and the addition of $^{125}$I labeled F(ab')$_2$ of affinity purified goat anti-mouse IgG antibodies as described previously. The addition and incubation with fresh SN10 was necessary for determining gp36 on the control IgG treated DND-39. Therefore, the same addition and incubation with fresh SN10 was carried out with the SN10 treated DND-39. Also, we carried out a control experiment in which fresh SN10 was not added. In this experiment, the $^{125}$I labeled F(ab')$_2$ of affinity purified goat anti-mouse IgG antibodies were added to the DND-39 cells which had been previously incubated with an excess of SN10 and washed. The result of this control test was almost identical to that of the above test in which fresh SN10 was added.

As a positive control, an excess of mAb SN5 defining CD10 (CALLA) was incubated with NALM-6 cells as described previously.

Preparation of Immunotoxin.

The purified mAb and an isotype matching control mouse IgG (IgG1) were individually conjugated to ricin A chain as previously described by Hara et al., Cancer Res., 48, 4673–4680 (1988). The conjugates were purified by gel filtration on a calibrated Sephacryl S-300 column as described by Hara et al. followed by affinity chromatography on a Blue Sepharose column as described by Knowles et al., Anal. Biochem. 160, 440–443 (1987).

Determination of Activity of Immunotoxin.

The in vitro cytotoxic activity of immunotoxin was determined by two different methods, i.e., a protein synthesis inhibition assay and a direct test of cytotoxicity against LL cells and control cells (Seon et al., Cancer Res. 44, 259–264 [1984]). The present procedure of the protein synthesis inhibition assay is briefly described below.

DND-39, a gp36 expressing lymphoma cell line, or MOLT-4, a gp36 negative T ALL cell line, was incubated, in triplicate, with varying concentrations of SN10-RA or control IgG-RA for 24 hours. The incubated cells were centrifuged, washed, and resuspended in leucine-free medium containing 1 μCi of [$^3$H]leucine. The cell suspension was incubated for 4 hours and centrifuged, and the pelleted cells were washed. The cells were harvested on glass fiber filters using a multiple semiautomatic cell harvester (type 7010; Skatron Inc., Sterling, Va.), and the $^3$H radioactivity was determined in a liquid scintillation spectrometer. Protein synthesis in the conjugate treated cells is expressed as the percentage of [³H]leucine incorporated into control cells not exposed to conjugate.

RESULTS

Initial Characterization of mAb.

Reactivity of culture supernatants of 48 hybridoma primary cultures and hybridoma clones derived from the selected primary cultures were initially characterized using a cellular RIA with various cultured and uncultured cells.

Based on these test results, the mAb termed SN10, which was produced by the hybridoma clone 2B-4G9, was chosen for further studies. The properties of SN10 are described herein. SN10 was found to be an IgG1-$k$ antibody. The reactivity of SN10 with various human LL cell lines and EB virus transformed nonmalignant cell lines is summarized in Table 1. SN10 reacted with all of the 10 mature B LL cell lines tested. In addition, SN10 reacted with 2 (i.e., REH and KM-3) of the 3 immature non-T/non-B (B-cell lineage) LL cell lines, one (i.e., NALM-1) of the 2 immature pre-B LL cell lines, and two (i.e., ARH-77 and HS) of the 3 plasma cell lines tested. However, SN10 did not react significantly with T, myelo/monocytic, and myeloerythroid LL cell lines (Table 1).

SN10 showed a weak but definite reactivity against 3 EB virus transformed nonmalignant B-cell lines. It should be noted, however, that EB virus is absent in many of the SN10 reactive LL cell lines, e.g., REH, KM-3, NALM-1, and SU-DHL-4 (Minowada et al., Advances in Malignant Lymphomas: Etiology, Immunology, Pathology, Treatment, pp. 53–74, New York: Academic Press, Inc., 1982).

Reactivity of SN10 with Fresh (Uncultured) LL Cells.

Reactivity of SN10 with uncultured LL cells was routinely determined by a cellular RIA and, in selected cases, also by FACS analysis. The results of a cellular RIA with uncultured LL specimens from 68 different LL patients are summarized in FIG. 1. The test results are consistent with those obtained using cultured LL cell lines (Table 1). SN10 reacted with all but one of mature B LL cell specimens tested. SN10 reacted with all of the 17 B NHL, all of the 15 B CLL, both of the 2 B prolymphocytic leukemia, all of the 3 B hairy cell leukemia, and 2 of the 3 B ALL specimens tested.

However, it should be noted that generally the reactivity of SN10 with uncultured B LL cell specimens is stronger than with cultured B LL cell lines.

SN10 did not react significantly with T NHL, T CLL, or T ALL specimens. With a few exceptions, non-T/non-B (including pre-B) ALL specimens did not react or reacted only marginally with SN10. SN10 reacted with 3 of the 6 acute myelocytic, or myelomonocytic leukemia specimens tested.

Figure 2:
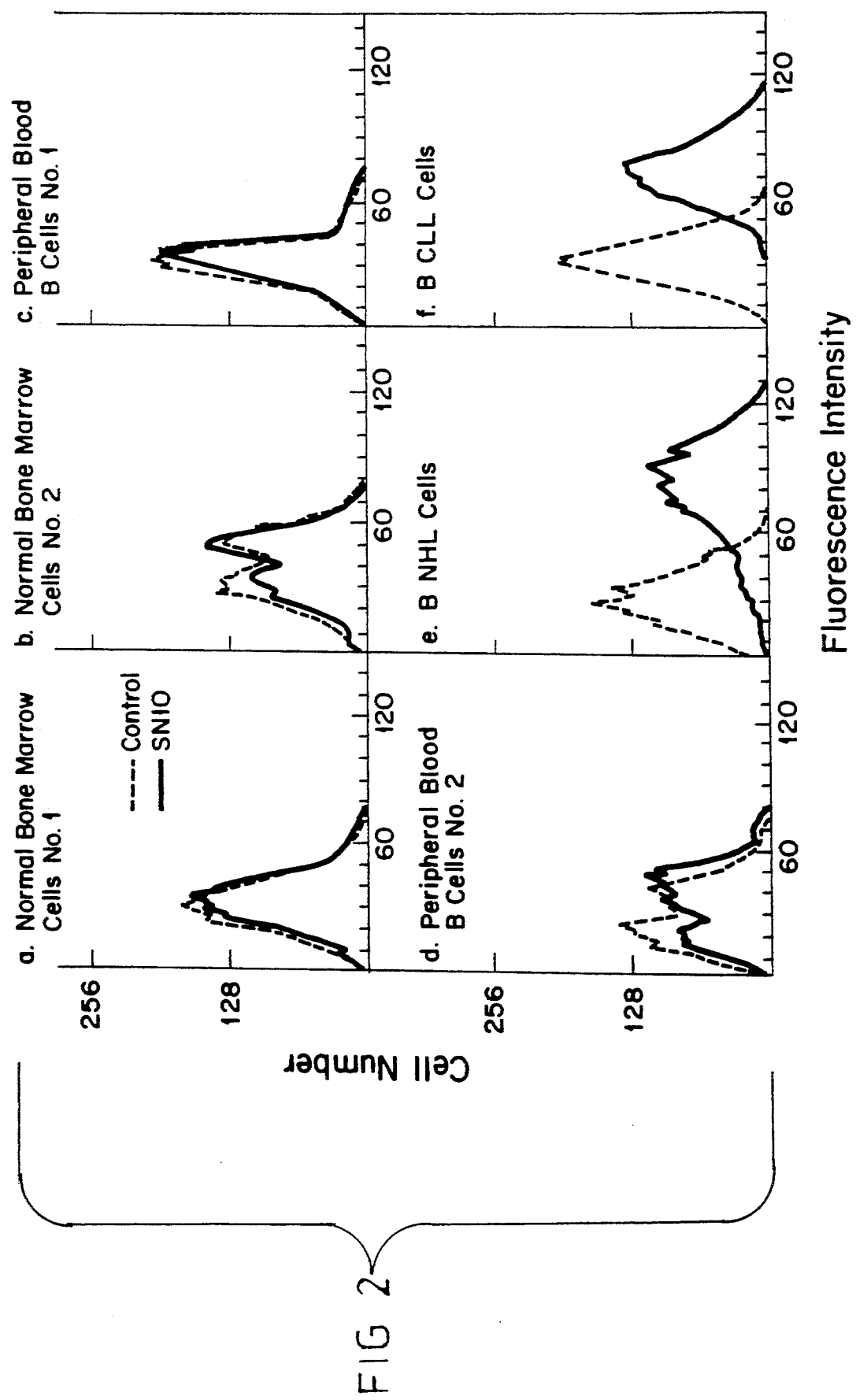
FIG. 2. FACS analysis of SN10 reactivity with various human cells. Target cells were allowed to react with SN10 or an isotype matching control mouse IgG (MOPC 195variant; IgG1-$k$) and stained with fluorescence conjugated F(ab')$_2$ of sheep anti-mouse immunoglobulin antibodies. The two bone marrow specimens shown were obtained from two different ALL patients in remission, and mononuclear cells were isolated for use in the test. The two B-cell specimens were individually isolated from peripheral blood of two healthy donors. The B NHL and B CLL specimens were uncultured cell specimens. The fluorescence intensity is on a log scale.

An example of FACS analysis with a B NHL and a B CLL specimen is shown in FIG. 2. The majority (77 and 72%, respectively) of the B NHL and B CLL specimens reacted with SN10.

Reactivity with Uncultured Normal Cells.

B cells, T cells, monocytes, granulocytes, erythrocytes, and platelets were isolated from peripheral blood of three healthy donors and tested for reactivity with SN10 by a cellular RIA. SN10 showed a weak marginal reactivity with B cell specimens but no significant reactivity with other cell specimens. Therefore, the reactivity of SN10 with B cells was further tested by FACS analysis. The FACS analysis results of 2 of the 3 specimens tested are shown in FIG. 2. A weak marginal reactivity of SN10 was detected with a minor subpopulation (<1, 2.7 and 3.9%) of the B cell preparations derived from the three different donors. One of these B cell preparations was tested for its reactivity with an anti-HLA-DR mAb (monomorphic; Becton Dickinson) by FACS analysis. The test showed that 77.5% of the B-cell preparation reacted with the anti-HLA-DRmAb.

To further characterize the specificity of the mAb, SN10 was tested for its reactivity with normal (or nearly normal) bone marrow specimens by FACS analysis; these bone marrow specimens were obtained from 5 different LL (4 ALL and one acute myelocytic leukemia) patients in remission. FACS analysis results of 2 of the 5 bone marrow specimens are shown in FIG. 2. Reactivity of SN10 with these 5 normal bone marrow specimens was not detectable (<1% for 2 specimens) or marginal (approximately 1% for the 3 other specimens). These bone marrow samples were tested for their reactivity with an anti-HLA-DR mAb (monomorphic) by FACS analysis. The tests showed that 20.8, 25.7, 27.9, 11.3 and 18.6% of these samples reacted with the anti-HLA-DR mAb.

Reactivity with Solid Tissues as Determined by Immunohistochemical Staining.

Figure 3A:
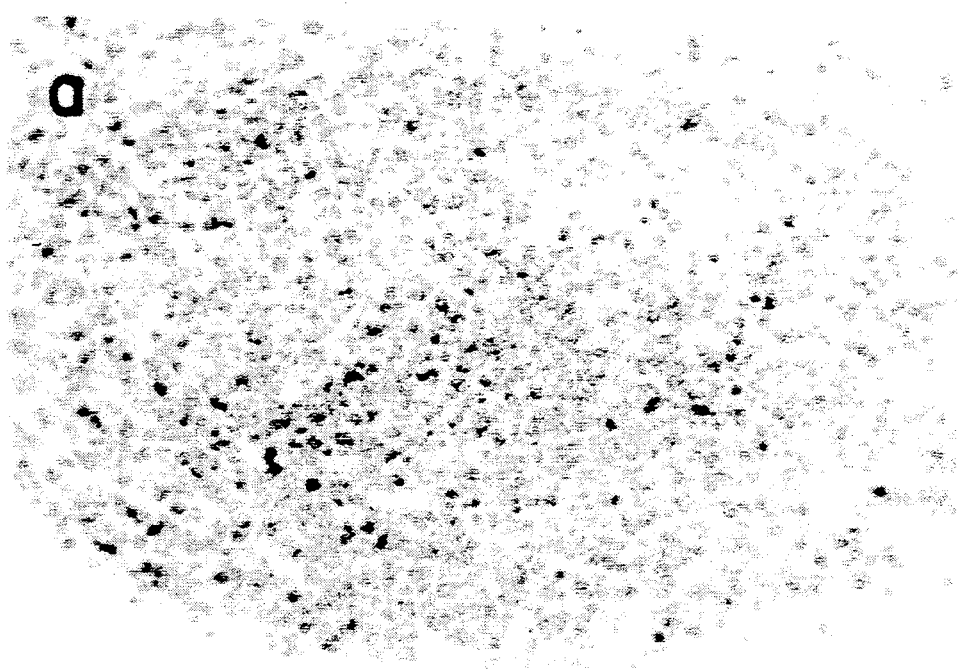
Figure 3B:
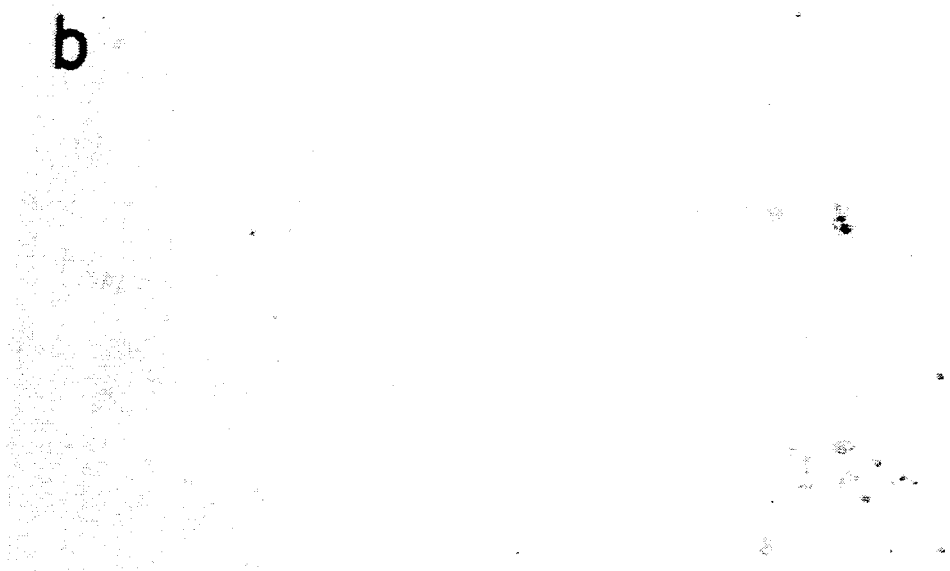

Immunohistological assays performed on frozen sections showed good reactivity of SN10 with malignant lymph nodes from four B NHL patients tested. Reactivity of SN10 with two of these NHL lymph node samples are illustrated in FIG. 3; these two are lymph nodes involved by follicular small cleaved cell lymphoma (FIG. 3a) and diffuse small cleaved cell lymphoma (FIG. 3c). An isotype matching control murine IgG (IgG1) did not show significant reaction with the NHL samples except for a focal reaction due to endogeneous peroxidase and example is shown in FIG. 3b. SN10 showed varying patterns of reactivity with hyperplastic reactive lymph nodes from three donors. An example is shown in FIG. 3d; sparse to moderate numbers of the germinal center and interfollicular cells are SN10 positive, while the majority of follicular mantle zone cells are SN10 positive. G4-3A7 (anti-HLA-DR), an isotype matching positive control mAb, reacted strongly with both germinal center and mantle zone cells and moderately with the interfollicular cells of the same reactive lymph node.

No significant reactivity with SN10 was noted in normal epidermis, lung, kidney, or small intestinal mucosa.

Determination of Circulating Antigens in the Plasma of Patients.

Figure 4:
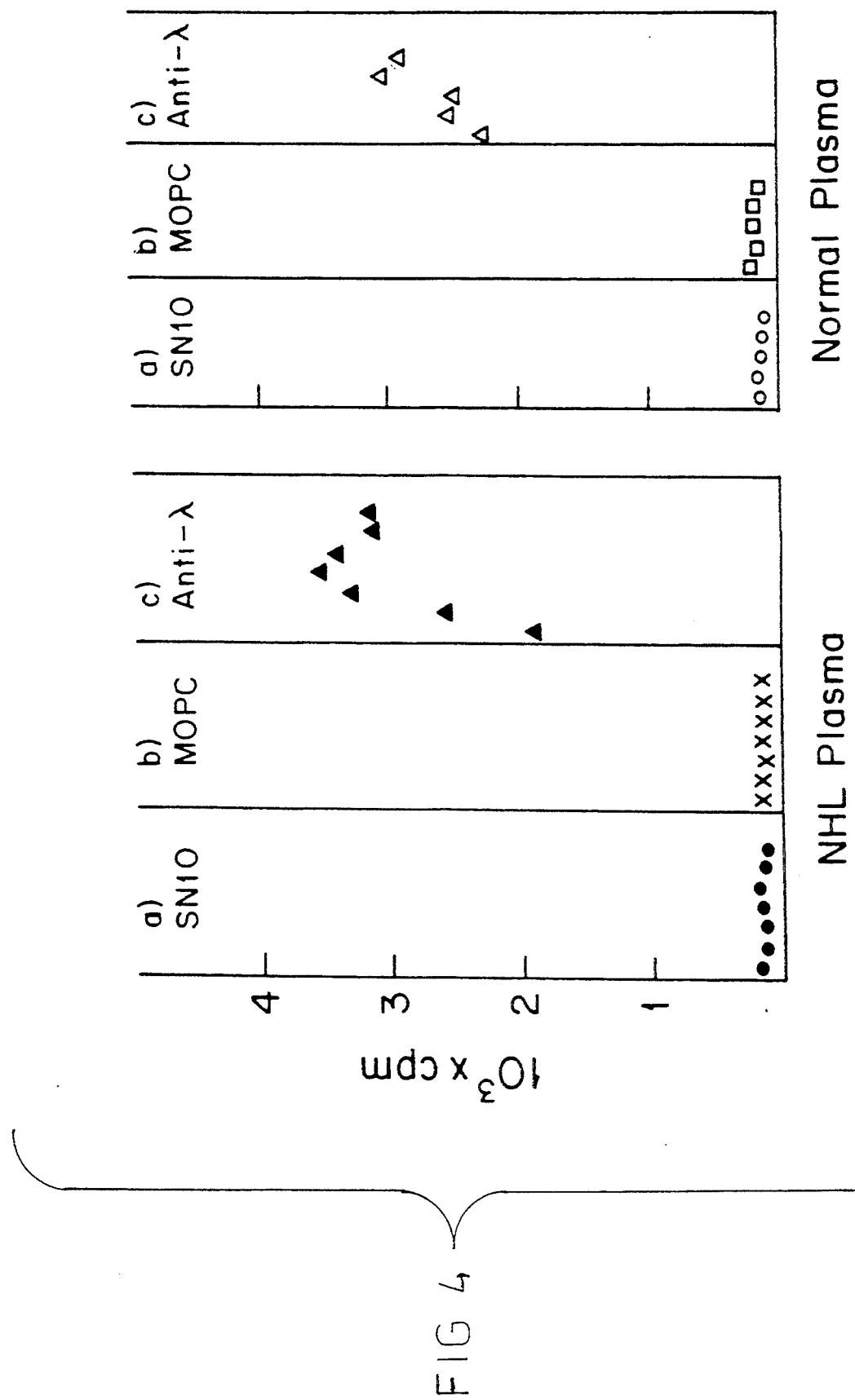
FIG. 4. Absence of gp36 in the plasma of LL patients and healthy individuals. A solid phase RIA was used to determine circulating gp36 in the plasma of 7 B NHL patients, 7 B CLL patients, and 5 healthy individuals. An isotype matching control IgG (MOPC 195variant) and anti-human immunoglobulin λ chain mAb (IgG1) were used along with SN10 as a negative and a positive control. gp36 was not detectable in any of the tested specimens. Therefore, only the results of NHL (4A) and healthy control (4B) specimens are shown. A titration experiment was carried out separately to determine the sensitivity of the RIA for detecting gp36. (See Components and Procedures for Reactions and Testing.)

Circulating antigen in the plasma of patients may bind an administered mAb and thereby inhibit the therapeutic efficacy of the administered mAb and immunoconjugate. Therefore, we tested for circulating SN10 antigen in the plasma of LL patients and healthy individuals (control) by using a solid phase RIA. A titration experiment showed that this RIA allows us to detect SN10 antigen contained in as little as 1 µg of total crude cell membrane protein preparation from B NHL cells. No significant amount of SN10 antigen was detected in any of the plasma samples derived from 7 different B NHL patients (FIG. 4A) and 5 different healthy individuals (FIG. 4B). Similarly, no significant SN10 antigen was detected in the plasma samples derived from 7 different B CLL patients.

Molecular Nature of Antigen.

Cell membranes were prepared from a mixture of malignant cells from two B NHL patients. Cell membranes were also prepared from malignant cells of a B CLL patient as well as of a B prolymphocytic leukemia patient. Glycoproteins were isolated separately from each of the three cell membrane preparations and radiolabeled individually with $^{125}$I.

The immunoprecipitates obtained by using the radiolabeled samples and SN10 (IgG1.$_k$), an isotype matching control mouse IgG, or control mAbs were analyzed by SDS-PAGE and autoradiographs were prepared. Some of the results are shown in FIG. 5.

Figure 5:
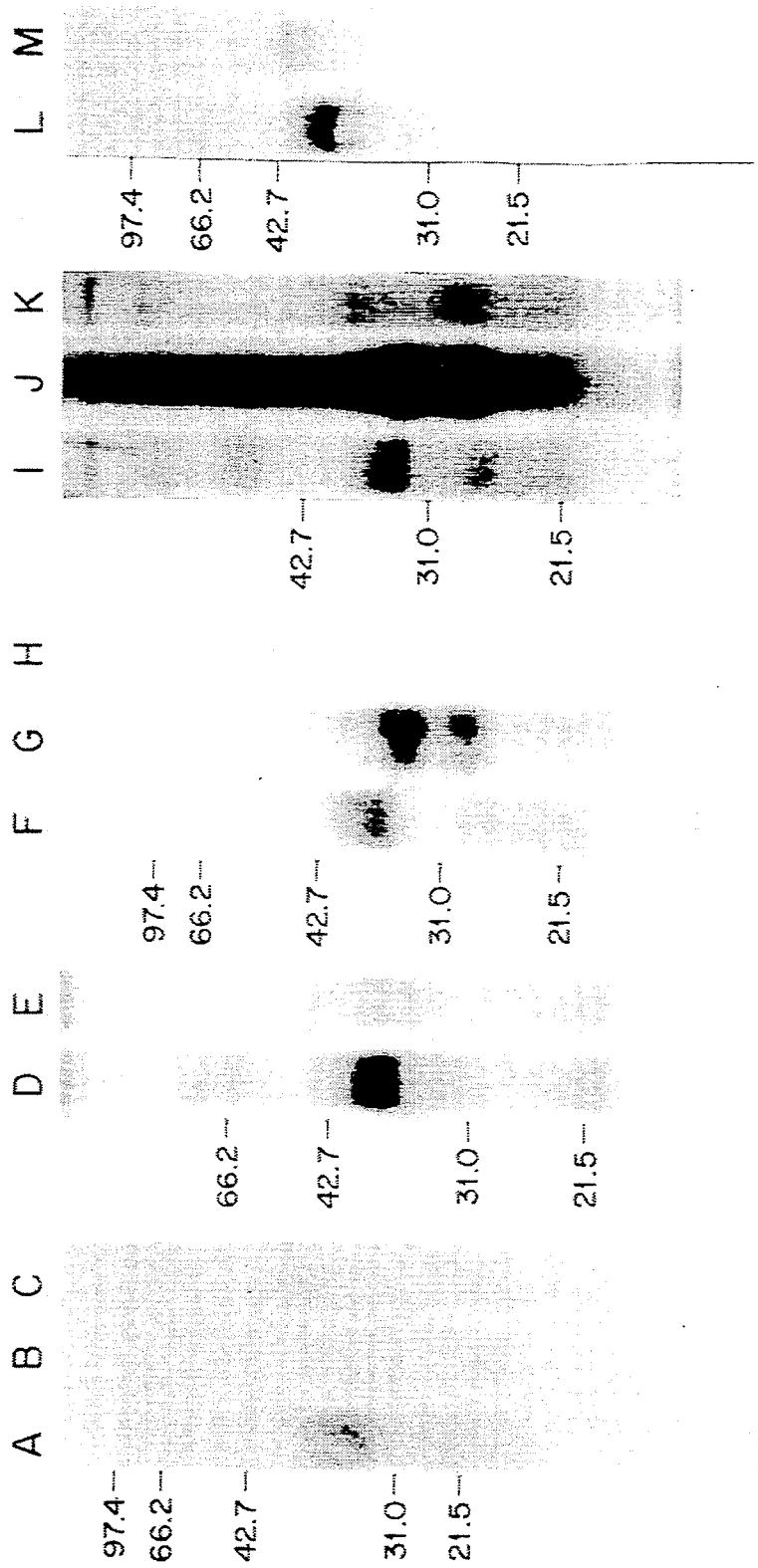
FIG. 5. SDS-PAGE of SN10 immunoprecipitates from $^{125}$I labeled cell membrane glycoprotein preparations obtained from two B NHL patients (lanes A–E), a B CLL patient (lanes F–K), and a B prolymphocytic leukemia patient (lanes L and M). In the immunoprecipitation, we used SN10 (lanes A, D, F, I and L), Leu 16 (an anti-CD20 mAb; lane B), control IgG (MOPC 195variant;lanes C, E, H, K and M), and anti-HLA-DR mAb (lanes G and J). Samples were analyzed after being reduced with dithiothreitol (lanes A, B, C, F, G, H, L and M) or unreduced (lanes D, E, I, J and K). Ordinate, Bio-Rad M$_r$ marker proteins were used after reduction as references.

The results of the NHL sample are shown in FIG. 5, lanes A–E. Under reduced conditions, the SN10 immunoprecipitate showed a single component of approximately $M_r$ 36,000 (lane A), whereas no significant component was immunoprecipitated by an isotype matching mAb Leu 16 (anti-CD20 mAb; lane B) or by an isotype matching control mouse IgG (MOPC 195variant; lane C). Under unreduced conditions, the SN10 immunoprecipitate showed a single component with a molecular size similar to that of the reduced antigen (lane D), whereas the control IgG immunoprecipitate did not show any significant component (lane E).

Therefore, the SN10 antigen is a glycoprotein with an approximate $M_r$ of 36,000 and consists of a single polypeptide chain.

This conclusion was supported by the following results obtained with a B CLL sample (lanes F–K) and a B prolymphocytic leukemia sample (lanes L and M). Under reduced conditions with the CLL sample, SN10 immunoprecipitated a single component of $M_r$ 36,000 (lane F), whereas anti-HLA DR mAb, a control mAb, immunoprecipitated two components of 33,000 ($\alpha$ chain) and 28,000 daltons ($\beta$ chain) (lane G). The control IgG immunoprecipitated no significant component (lane H). Essentially, the same results were obtained with the CLL sample under unreduced conditions (lanes I–K).

With a B prolymphocytic leukemia sample, SN10 immunoprecipitated an $M_r$ 36,000 component (lane L), whereas the control IgG precipitated only a minor nonspecific component (lane M).

Thus an $M_r$ 36,000 antigen was specifically immunoprecipitated by SN10 from each of the three samples tested, i.e., a B NHL, a B CLL, and a B prolymphocytic leukemia sample. The SN10 antigen was designated gp36.

Biochemical Nature of Epitope.

Daudi, a Burkitt's lymphoma cell line (Table 1), which expresses gp36 on the cell surface, was treated with trypsin and mixed glycosidases, and the antigenic determinant remaining on the treated cells was tested for by means of a cellular RIA. As a control, a mAb L1-1E5-2C8 which defines an epitope containing sialic acid(s) of the CD24 antigen was used (Seon et al., Mol. Immun. 23, 569–580 [1986] and Fukukawa et al., Exp. Hematol., 14, 850–855 [1986]). The results are shown in Table 2. The epitope defined by SN10 was strongly reduced by treatment with trypsin but not effected by treatment with mixed glycosidases. Treatment with the same glycosidases as well as trypsin substantially reduced the epitope defined by the control mAb L1-1E5-2C8. It should be noted that, on the cells, carbohydrates are attached to protein moieties which interact with the lipid bilayers of cell membranes. Therefore, carbohydrate as well as the protein moieties of a glycoprotein on cell surfaces may be eliminated by proteolytic digestion as in the case for the sialic acid defined by L12-1E5-2C8.

In conclusion, the present data suggest that SN10 epitope is primarily composed of the protein moiety of the glycoprotein antigen on Daudi cells.

Antibody Avidity and Number of Available Epitopes on LL Cells.

Scatchard plot analysis of direct binding of radiolabeled SN10 to an uncultured B NHL cell specimen, an uncultured B CLL cell specimen, and cultured DND-39 cells showed equilibrium constants of 5.2, 5.8, and 6.8×10$^8$ liters/mol, respectively. In the same analyses, the average number of antibody molecules bound/cell was estimated to be 7.4, 2.9, and 2.1×10$^4$, respectively, at the antibody saturation for the NHL, CLL, and DND-39 cells. Since SN10 (IgG1) is a bivalent antibody, the average number of antigens on these cell specimens is probably 1- to 2-fold of the above number of antibodies.

Thus, SN10 shows a high binding avidity to each of the three B LL cell specimens tested, and the SN10 antigen is expressed relatively abundantly on these cell specimens.

Regulation of Antigen Expression.

Binding of antibody to a cell surface antigen may induce antigenic modulation and down-regulation of antigen biosynthesis and expression (Luo et al., J. Immunol., 145, 1974–1982 [1990]). However, binding of SN10 to gp36 on DND-39 cells did not cause significant down-regulation of antigen expression as determined by a cellular RIA (FIG. 6; Components and Procedures for Reaction and Testing.)

Nevertheless, mAb SN10 is effectively internalized into the LL cells after binding as demonstrated by the effective killing of the LL cells by the RA conjugate of SN10.

Specific Killing of LL Cells by RA Conjugate of SN10.

Figure 7A:
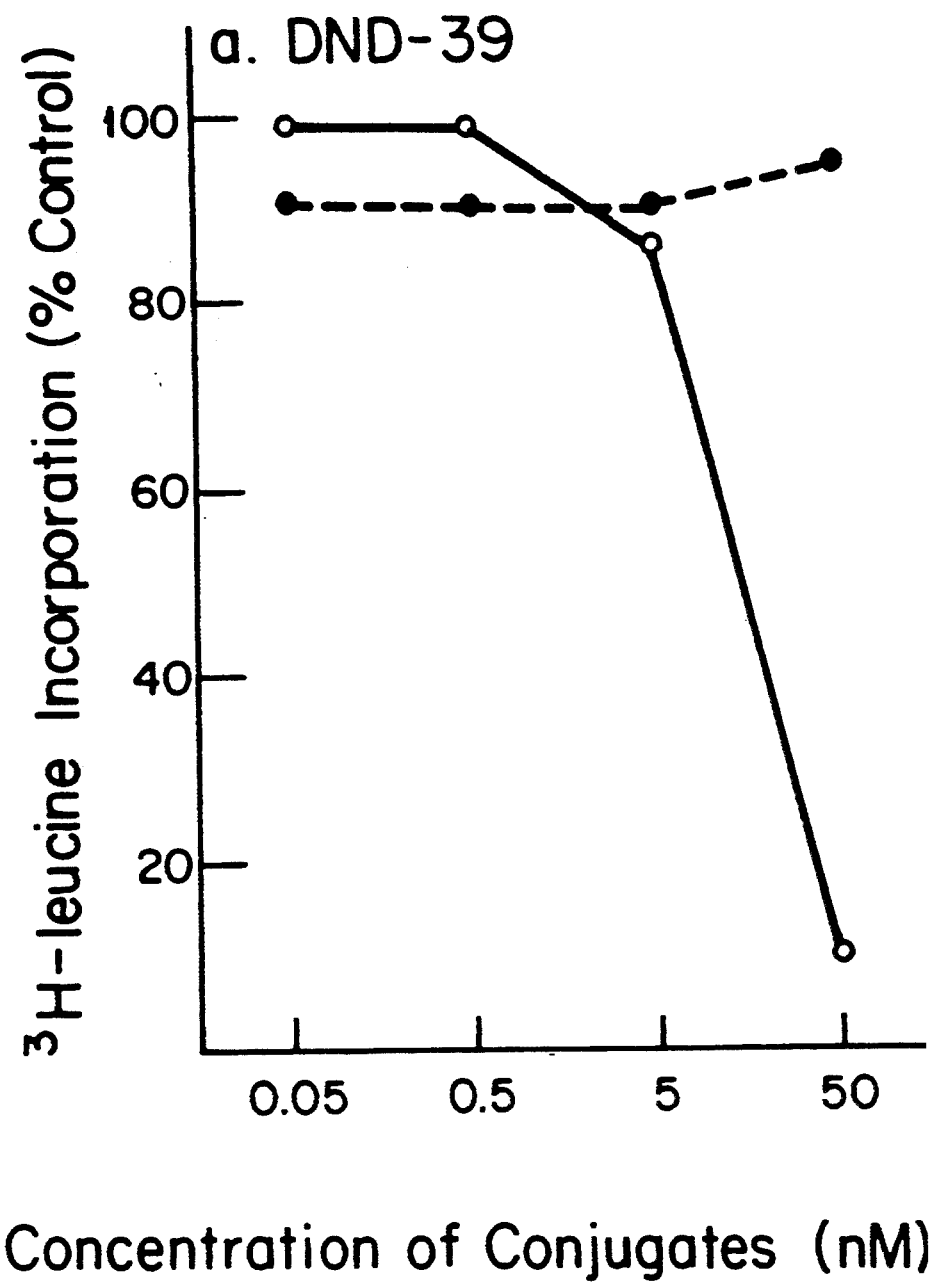
FIGS. 7A–7B. Specific inhibition of protein synthesis in gp36 expressing DND-39 by ricin A chain conjugate of SN10. DND-39, FIG. 7A, or MOLT-4, FIG. 7B, a gp36 negative T ALL cell line, was incubated with varying concentrations of SN10-RA or control IgG-RA and labeled with [$^3$H]leucine (see Components and Procedures for Reactions and Testing for details). Protein synthesis in the conjugate treated cells is expressed as the percentage of [$^3$H]leucine incorporated into control cells not exposed to conjugate.
Figure 7B:
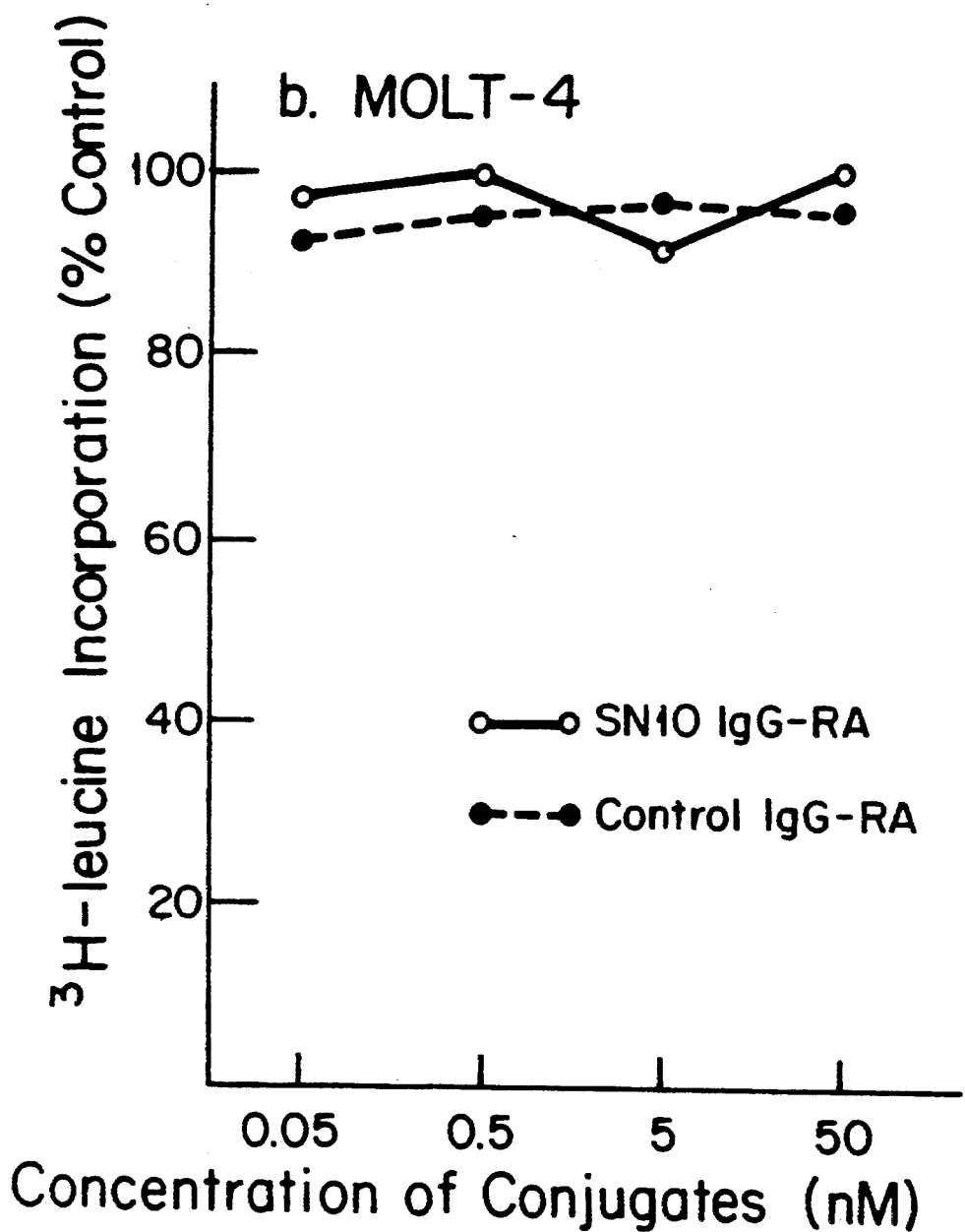

Specific cytotoxic activity of the RA conjugate of SN10 was tested against gp36 expressing LL cells and gp36 negative control cells using two different in vitro assays, i.e., a protein synthesis inhibition assay and a direct cytotoxicity test (see components and Procedures for Reactions and Testing). The results obtained by using the first assay procedure are shown in FIG. 7. The SN10-RA conjugate showed significant inhibition of protein synthesis against gp36 expressing DND-39 at concentrations >5 nM but not against gp36 negative MOLT-4. The control IgG-RA conjugate showed no significant inhibitory activity against either DND-39 or MOLT-4. In the above test, no immunotoxin potentiator such as NH$_4$Cl was added. Addition of 10 mM NH$_4$Cl potentiated the specific cytotoxicity of SN10-RA by approximately 10-fold (data not shown). Results consistent with the above were obtained for the specific cytotoxic activity of SN10-RA by using the second assay procedure, i.e., a direct cytotoxicity test.

Thus, SN10-RA is effective in specific killing of gp36 expressing LL cells. Furthermore, the present results indicate that mAb SN10 is effectively internalized into target LL cells after binding to the cell surface antigen.

DISCUSSION

In the past several years, a number of investigators reported many mAbs which reacted with human normal and malignant B cells (reviewed in Refs: Zola, Immunol. Today, 8, 308–315 [1987] and Clark et al., Adv. Cancer Res. 52, 81–149 [1989]). However, only a small number of these mAbs show a highly selective reactivity with malignant B cells over normal B cells.

A new mAb SN10 which was generated and characterized in this study shows a highly selective reactivity with malignant B-cells. Furthermore, SN10 appears to be different from those previously reported mAbs in the antibody specificity and/or in the molecular nature of the antigen defined. The antigen defined by SN10 appears to be different from any of the reported CD series antigens (Knapp et al., Immunol Today, 10, 253-258 [1989]).

The antigen defined by SN10 is a cell surface glycoprotein composed of a single polypeptide chain of $M_r$ 36,000 and designated gp36. The epitope defined by SN10 appears to be primarily composed of the protein moiety of gp36 on Daudi lymphoma cells. In general, gp36 is expressed to a greater degree on fresh (uncultured) LL cells than on cultured LL cell lines. gp36 may be a transformation associated antigen because (a) SN10 strongly reacts with malignant B LL cells, (b) SN10 shows a weak marginal reaction with a few percent (e.g., <1, 2.7, and 3.9%) of normal peripheral blood B-cells, (c) SN10 does not react significantly with normal bone marrow cells, (d) SN10 reacts with EB virus transformed nonmalignant B-cell lines as well as EB virus negative LL cell lines, and (e) SN10 shows varying patterns of reactivity with the hyperplastic reactive lymph nodes.

mAb SN10 was generated using an unconventional approach, i.e., immunizing animals (mice) with an LL antigen preparation rather than intact LL cells. Previously we developed a novel system for isolating immunologically active LL associated cell membrane antigen mixtures. Using such antigen preparations isolated from T and non-T/non-B (immature B-lineage including pre-B) LL cells to immunize mice, we previously generated several mAbs directed to T or non-T LL associated cell surface antigens. In the present study, we extended these studies and prepared a B LL associated cell membrane antigen preparation from mononuclear cells derived from malignant spleens of two patients with B NHL. SN10 was generated by immunizing mice with this antigen preparation.

Several mAbs reactive with normal and malignant B-cells have been widely used for diagnosis and follow-up of LL (reviewed in Foon et al., Blood, 68, 1-31 [1978]). SN10 is particularly useful for such purposes because it reacts strongly with many malignant cells and tissues of B-lineage but shows little reactivity with normal counterparts, i.e., normal peripheral blood B-cells and normal bone marrow B-cells. SN10 showed no significant reactivity with a variety of other normal cells and normal solid tissues tested. The normal cells include T cells, granulocytes, monocytes, erythrocytes, and platelets. The normal solid tissues include epidermis, kidney, lung, and small intestine. Thus, SN10 shows remarkably high tumor specificity.

SN10 may be useful for studying the tumorigenetic mechanisms in LL. Another important application of antitumor mAbs is the utilization of mAbs as a specific delivery vehicle of a cytotoxic agent(s) to tumor targets.

However, only those mAbs which meet several fundamental criteria mentioned before and below, may have potential for an effective delivery vehicle. These criteria include relatively high tumor specificity, high antigen binding affinity, high antigen density, effective internalization into the target cells, noninduction of down-regulation of antigen expression, and lack of circulating antigen in the plasma of patients. SN10 appears to meet these fundamental requirements to serve as an effective delivery vehicle.

As an initial test for the usefulness of SN10 for preparing immunoconjugates, SN10 was conjugated with RA, and the in vitro cytotoxic activity of SN10-RA was determined. SN10-RA killed LL cells effectively, whereas the same conjugate showed no cytotoxicity against control cells (FIG. 7). Thus, SN10 bound to the target antigen (gp36) on LL cells was effectively internalized into the cells. However, the binding of mAb SN10 to LL cells did not cause significant down-regulation of gp36 expression as assayed by our test procedure (FIG. 6; Components and Procedures for Reactions and Testing).

Another important use of SN10 will be radioimmunodetection and radioimmunotherapy of NHL after SN10 is conjugated to an appropriate radioisotope because SN10 displays a remarkably high tumor specificity and is an IgG1 antibody. IgG1 antibodies show less nonspecific binding (e.g., binding to Fc receptors) than IgG2a, IgG3, and IgM antibodies.

TABLE 1

Reactivity of SN10 with LL cell lines and EB virus transformed nonmalignant cell lines
The reactivity of SN10 was determined using 20 μl of culture fluid of SN10 hybridoma and $2 \times 10^5$ cells by means of a cellular RIA. Each test was carried out in triplicate and the values given are the means ± SD.

| Cell line | Origin of cell line | Reactivity (cpm) SN10 | Control IgG[a] |
|---|---|---|---|
| LL non-T/non-B[b] | | | |
| REH | ALL | 1354 ± 137 | 256 ± 54 |
| KM-3 | ALL | 1308 ± 122 | 356 ± 72 |
| NALM-16 | ALL | 346 ± 48 | 238 ± 88 |
| LL Pre-B | | | |
| NALM-1 | CML-BC[c] | 943 ± 112 | 323 ± 38 |
| NALM-6 | ALL | 390 ± 69 | 253 ± 28 |
| LL B | | | |
| BALL-1 | ALL | 780 ± 109 | 316 ± 36 |
| BALM-2 | ALL | 1602 ± 57 | 282 ± 15 |
| BALM-3 | Lymphocytic lymphoma | 741 ± 54 | 356 ± 1 |
| BALM-5 | Lymphocytic lymphoma | 780 ± 208 | 277 ± 12 |
| SU-DHL-4 | Histiocytic lymphoma | 1697 ± 166 | 272 ± 51 |
| DND-39 | Burkitt's lymphoma | 1554 ± 102 | 174 ± 20 |
| Daudi | Burkitt's lymphoma | 1920 ± 351 | 305 ± 14 |
| Raji | Burkitt's lymphoma | 796 ± 149 | 269 ± 39 |
| Ogun | Burkitt's lymphoma | 443 ± 65 | 143 ± 12 |
| Chevalier | Burkitt's lymphoma | 1823 ± 105 | 450 ± 166 |
| Plasma | | | |
| ARH-77 | Multiple myeloma | 961 ± 18 | 132 ± 40 |
| RPMI 8226 | Multiple myeloma | 285 ± 51 | 419 ± 120 |
| HS | Multiple myeloma | 581 ± 54 | 238 ± 31 |
| LL T | | | |
| MOLT-4 | ALL | 271 ± 42 | 256 ± 54 |
| JM | ALL | 311 ± 91 | 223 ± 64 |
| CCRF-HSB-2 | ALL | 221 ± 31 | 203 ± 30 |
| HPB-MLT | LTL | 322 ± 35 | 216 ± 29 |
| LL myelo/monocytic | | | |
| HL-60 | APL | 327 ± 22 | 244 ± 30 |
| U937 | Histiocytic lymphoma | 339 ± 18 | 200 ± 12 |
| LL myelo-erythroid | CML-BC | 195 ± 12 | 156 ± 34 |
| K562 | | | |
| EB virus transformed | | | |
| CCRF-SB | | 703 ± 162 | 205 ± 26 |
| RPMI 1788 | | 693 ± 84 | 261 ± 95 |

TABLE 1-continued

Reactivity of SN10 with LL cell lines and EB virus transformed nonmalignant cell lines The reactivity of SN10 was determined using 20 μl of culture fluid of SN10 hybridoma and 2 × 10⁵ cells by means of a cellular RIA. Each test was carried out in triplicate and the values given are the means ± SD.

| | | Reactivity (cpm) | |
|---|---|---|---|
| Cell line | Origin of cell line | SN10 | Control IgG[a] |
| RPMI 8057 | | 692 ± 77 | 184 ± 13 |

[a]Purified mouse plasmacytoma IgG1 (MOPC 194 variant) was dissolved in the hybridoma culture medium at a concentration of 10 μg/ml.
[b]B-cell lineage.
[c]CML-BC. chronic myelogeneous leukemia in blast crisis: LTL. leukemic phase of T-cell lymphoma APL. acute promyelocytic leukemia.

TABLE 2

Binding of mAbs to enzyme treated LL cells

Daudi cells (see Table 1) were incubated, in triplicate, at 37° C. for 1 h in the presence or in the absence (control) of the specified enzymes, and the individual cell samples were tested for the binding activity with SN10 by means of a cellular RIA.

| | | Reduction in antibody binding by enzyme treatment (%) | |
|---|---|---|---|
| Enzyme[a] | | SN10 | L1-1E5-2C8 (control)[b] |
| Trypsin | 0.1 | 56.5 | 88.2 |
| | 1.0 | 85.9 | 90.6 |
| Mixed glycosidases | 0.01 | −0.013 | 13.1 |
| | 0.1 | −0.049 | 35.7 |

[a]The amount of enzymes is mg/ml.
[b]As a reference, the results of mAb L1-1E5-2C8 directed to neuraminic acid residue(s) of the CD24 antigen (34) are included. For L1-1E5-2C8, KM-3 cells (see Table 1) were incubated as described above. L1-1E5-2C8 reacts poorly with Daudi cells.

What is claimed is:

1. A monoclonal antibody, or fragments thereof, produced by hybridoma cell line 2B-4G9, having ATCC designation number HB 11101 or subclones thereof which react with representatives from each of the leukemia lymphoma cell specimens selected from the group consisting of B non-Hodgkin's lymphoma cells, B chronic lymphocytic leukemia cells, B prolymphocytic leukemia cells, B hairy cell leukemia cells, and B acute lymphoblastic leukemia cells.

2. Fragments of the monoclonal antibody of claim 1 wherein the fragments are selected from the group consisting of F(ab')₂, Fab', Fab, Fv, Fd', and Fd.

3. A method for detecting the presence of leukemia or lymphoma cells in a patient which comprises contacting an appropriate biological specimen of said patient with a measured amount of the monoclonal antibody or monoclonal antibody fragments of claim 1 and analyzing for a reaction between said monoclonal antibody and the patient's specimen.

4. A hybridoma cell line designated 2B-4G9, having ATCC designation number HB 11101.

* * * * *